(12) United States Patent
Sin et al.

(10) Patent No.: US 7,030,265 B2
(45) Date of Patent: Apr. 18, 2006

(54) RETINOL DERIVATIVES, THE METHOD OF PREPARATIONS AND THE USES THEREOF

(75) Inventors: Hong-Sig Sin, Seoul (KR); Si-Ho Park, Jeonju (KR); Young-Soy Rho, Jeonju (KR); Soo-Jong Um, Seongnam (KR); Youn-Ja Kwon, Seoul (KR); Myoung-Soon Park, Eujeongbu (KR); Hye-Sook Han, Seoul (KR); Min-Sook Jung, Jeonju (KR); So-Mi Kim-Cho, Namyangju (KR); Dong-Myong Kim, Seoul (KR); Deok-kun Oh, Kwachun (KR); Jong-Sup Park, Seoul (KR)

(73) Assignee: Chebigen, Inc., Seoul (KR)

( * ) Notice: Subject to any disclaimer, the term of this patent is extended or adjusted under 35 U.S.C. 154(b) by 466 days.

(21) Appl. No.: 10/221,428

(22) PCT Filed: Jan. 10, 2002

(86) PCT No.: PCT/KR02/00041

§ 371 (c)(1),
(2), (4) Date: Jan. 2, 2003

(87) PCT Pub. No.: WO02/055540

PCT Pub. Date: Jul. 18, 2002

(65) Prior Publication Data

US 2004/0023888 A1    Feb. 5, 2004

(30) Foreign Application Priority Data

| Jan. 11, 2001 | (KR) | ................................. 2001/1667 |
| Jan. 9, 2002 | (KR) | ................................. 2002/1178 |

(51) Int. Cl.
*C07C 69/07* (2006.01)
*C07C 69/52* (2006.01)
*C07C 69/527* (2006.01)
*C07C 69/587* (2006.01)

(52) U.S. Cl. ...................................... 560/129; 560/155
(58) Field of Classification Search ................ 560/129, 560/155
See application file for complete search history.

(56) References Cited

U.S. PATENT DOCUMENTS 2,941,009 A * 6/1960 Weisier et al. ............... 568/668

* cited by examiner

*Primary Examiner*—Elvis O. Price
(74) *Attorney, Agent, or Firm*—Jones Day (57) ABSTRACT

The present invention relates to novel retinol derivatives, the methods of preparation and the uses thereof. According to the present invention, retinol derivatives comprise carboester linkage between di-, tri-, polypeptide having functional group of COOH and retinol. Retinol derivatives in the present invention comprise carboester linkage between amino acid having functional group of di-COOH and retinol. Retinol derivatives comprise carboester linkage between retinol and the compounds having the function group of COOH and multiple double bonds on carbon chain. Retinol derivatives in the present invention comprise carboester linkage between retinol and the compounds having the functional group of di-COOH and one double bond. Retinol derivatives in the present invention comprise ether linkage between the compounds with OH functional group and retinol.

14 Claims, 4 Drawing Sheets

(A) RAR Subtypes

(B) RXR Subtypes

[FIG. 3]

RO-Mesaconic-RO

| receptor | | retinoid | CAT | fold act. |
|---|---|---|---|---|
| RARα | a | control | 0.208 | 1.00 |
| | b | retinol | 0.62 | 2.98 |
| | c | RO-Mesaconic RO | 1.051 | 5.05 |
| RARβ | a | control | 0.654 | 1.00 |
| | b | retinol | 1.005 | 1.54 |
| | c | RO-Mesaconic RO | 1.187 | 1.81 |
| RARγ | a | control | 0.648 | 1.00 |
| | b | retinol | 1.313 | 2.03 |
| | c | RO-Mesaconic RO | 1.405 | 2.17 |

[FIG. 4]

RO-fumaric-RO

| receptor | | retinoid | CAT | fold act. |
|---|---|---|---|---|
| RARα | a | control | 0.208 | 1.00 |
| | b | retinol | 0.62 | 2.98 |
| | c | RO-fumaric-RO | 1.535 | 7.38 |
| RARβ | a | control | 0.654 | 1.00 |
| | b | retinol | 1.005 | 1.54 |
| | c | RO-fumaric-RO | 1.569 | 2.40 |
| RARγ | a | control | 0.648 | 1.00 |
| | b | retinol | 1.313 | 2.03 |
| | c | RO-fumaric-RO | 1.422 | 2.19 |

RETINOL DERIVATIVES, THE METHOD OF PREPARATIONS AND THE USES THEREOF

FIELD OF THE INVENTION

The present invention relates to novel retinol derivatives, the method of preparations and the uses thereof.

Retinol derivatives are essential for a foetal development of the animal, for homeostatis, for vision, for morphogenesis, for skin aging and for the control of the cell differentiation. Also, Retinol derivatives are considered to have the utility as the agent for the inhibition or treatment of the cancer caused by virus or the other factor due to the inhibition of cell reckless proliferation and the induction of cell differentiation or the induction of the apoptosis.

Retinol derivatives maintain the activity of the epithelial tissue and inhibit the skin aging indirectly by interrupt of the signal transmittance of the ultraviolet light. Differentiation of the stem cell to the muscle neuron cell depends on the concentration of the retinol. Therefore, retinol itself as well as its derivatives is widely used in the various fields such as medicine, cosmetics, etc.

BACKGROUND OF THE INVENTION

The methods of preparation of retinol via several stages are described in U.S. Pat. Nos. 4,035,425, 4,064,183, 4,092,366. However, pure retinol prepared by the above methods is unstable in the light, easily photoisomerized and degraded with consequence that its activity is affected and generally stabilizer is added into the commercial product of retinol.

Even though the methods of preparation of retinol derivatives bonded various carbohydrates are disclosed in U.S. Pat. Nos. 4,473,503 and 5,631,244 in order to overcome the stability problem cited above, the steps of the preparation are complex, non-economical and are not satisfactory in terms of the stability.

Accordingly, it is required the needs of retinol derivatives which are stable in the light and aqueous solution and of which the preparation method is simple and economical.

The present invention solves the above problems and the object of the present invention is to prepare novel retinol derivatives, the preparation method having high yields, and the uses thereof.

DETAILED DESCRIPTION OF THE INVENTION

The present invention relates to novel retinol derivatives, the methods of preparation and the uses thereof.

According to the present invention, retinol derivatives are carboester derivatives and ether derivatives of retinol.

Carboester derivatives of retinol in the present invention comprise carboester linkage between di-, tri-, polypeptide with COOH functional group and retinol Carboester derivatives in the present invention comprise carboester linkage between amino acid with di-COOH functional group and retinol.

According to the present invention, other carboester derivatives of retinol comprise carboester linkage between the compounds with COOH function group and multipe double bond on carbon chain and retinol.

Carboester derivatives of retinol comprise carboester linkage between the compounds with di-COOH functional group and one double bond and retinol.

Ether derivatives of retinol comprise ether linkage between the compounds with OH functional group and retinol.

In the following, the present invention will be explained in more detail.

According to the present invention, the structure of carboester derivatives of retinol is represented as follows. Among carboester derivatives of retinol in the present invention, representative example having carboester linkage between di-, tri-, polypeptide with COOH functional group and retinol corresponds to the following formula 1.

In the following formula 1, peptide with COOH functional group is selected from di-, tri-, polypeptide comprising of N-L-α-aspatyl-L-phenylalanine 1-methylester(APM; aspatam), N-protecting group-aspatam, neotam, etc.

Formular 1 wherein, $R^1$ is H, CHO, Retinoic acid(RA), Ac or Boc, $R^2$ is OH, $OCH_3$, $OC_2H_5$, Retinol, or CLA, n is integer of 1~6.

According to the present invention, the structure of carboester derivatives of retinol having carboester linkage between amino acid with di-COOH functional group and retinol corresponds to the following formula 2.

In the following formula 2, amino acid with di-COOH is selected from the group comprising aspartic acid, N-protecting group-aspartic acid, glutamic acid, N-protecting group-glutamic acid, α-aspatyl-L-phenylalanine(α-AP), N-protecting group-α-aspatyl-L-phenylalanine.

Formular 2 wherein, $R^1$ is H, CHO, Retinoic acid(RA), Ac or Boc, $R^2$ is OH, $OCH_3$, $OC_2H_5$, Retinol or CLA, n is the integer of 1~6.

According to the present invention, the structure of carboester derivatives of retinol having carboester linkage between the compounds with COOH functional group and multiple double bond on carbon chain and retinol corresponds to the following formula 3.

In the following formula 3, the compounds with COOH functional group and multiple double bond on carbon chain is selected from the group comprising oleic acid, linolenic acid, prodlure, leukotrienes, etc instead of conjugated linoleic acid (CLA).

Formular 3

According to the present invention, the structure of carboester derivatives of retinol having carboester linkage between the compounds with di-COOH functional group and one double bond and retinol corresponds to the following formula 4.

In the following formula 4, the compounds with di-COOH functional group and one double bond is selected from the group comprising maleic acid, fumaric acid, mesaconic acid, etc.

Formular 4 wherein, R is H, $CH_3$ or $C_2H_5$.

According to the present invention, the structure of ether derivatives of retinol having ether linkage between the compounds with OH functional group and retinol corresponds to the following formula 5.

In the following formula 5, the compounds with OH functional group is selected from the group comprising alkyl alcohol, aryl alcohol, dienyl alcol, trienyl alcohol, etc instead of retinol.

A method for preparing retinol carboester derivatives of the present invention consists of the following stages; 1) a converting stage of retinyl acetate to pure retinol by reacting retinyl acetate with an inorganic salt in the methanolic solvent and extracting retinol with ether, 2) a binding stage of the chemical selected from the group including the peptide comprising COOH, amino acid comprising di-COOH, the compounds containing functional group of COOH and multiple double bonds on the carbon chains, the compounds comprising the functional group of di-COOH and one double bond to retinol under the presence of a condensing agent and a catalyzing agent in the solvent, and 3) a separating, purifying and recovering stage of retinol carboester derivatives.

A method for preparing the retinol carboester derivatives of the present invention is explained by stages as follows;

At the first stage retinyl acetate, which is generally commercialized, is reacted with an inorganic salt in a methanolic solvent at 25–40° C. in the dark room to prevent photoisomerization during the reaction, and the reaction mixture is extracted with the ether solvent. At this time, an inorganic salt used is 1–3 equivalents and the extracting solvents comprises ethers such as diethylether or tetrahydrofuran(THF). The ether is used as a solvent because the residual inorganic salt dissolved in methanolic solvent reacts with the extracting solvents such like ethylacetate and converts to retinyl acetate.

At the second stage, a chemical selected from the group including the peptide comprising COOH, amino acid comprising di-COOH, the compounds containing functional group of COOH and multiple double bonds on the carbon chains, the compounds comprising the functional group of di-COOH and one double bond is reacted with condensing agent and methylene chloride (or organic solvent) to activate the acidity of the chemical or to convert to acyl halide. Thereafter the retinol carboesters are prepared by adding the pure retinol in the reaction mixture. The condensing agent comprises N,N'-dicyclohexylcarbodiimide (DCC), 1-ethyl-3-(3-dimethylaminopropyl) carbodiimide hydrochloride (EDCI), N,N'-carbonyldiimidazole (CDI), N,N'-sulfryldiimidazole (SDI)), SO2Cl and catalyzing agent which catalyze the condensing reaction comprises N,N'-dimethylaminopyridine (DMAP).

Formular 5

The third stage is separating the pure retinol carboester derivatives. The reaction mixture is column chromatographed on a special silicagel [Reverse-phase, Merck Silicagel 60 RP 18(40–63) μm].

A method for preparing the retinol ether derivatives consists of 1) converting stage of retinyl acetate to pure retinol, 2) binding stage of the chemical containing the functional group of OH and 3) separating, purifying and recovering stage of retinol ether derivatives.

A process for preparing the retinol ether derivatives of the present invention is explained by stages as follows;

At the first stage, generally commercially available retinyl acetate is reacted with an inorganic salt in methanolic solvent at 25–40° C. in the dark room to prevent photoisomerization and then the reaction mixture is extracted with the solvent such as ethers.

At the second stage, after the removal of solvent, a chemical containing the functional group of OH, a natural or isolated and purified retinol, Diethylazodicarboxylate (DEAD) and Triphenylphosphate(Ph3P) are added in the methylene solvent, and the reaction mixture is reacted at room temperature to prepare retinol ether derivatives.

The third stage is separating stage of the pure retinol derivatives. The reaction mixture is column chromatographed on a special silicagel [Reverse-phase, Merck Silicagel 60 RP 18(40–63) m].

Base, condensing agents and catalyzer are not limited to the aforementioned ingredients used in the method of preparing said retinol derivaties, and can extended any of the standard ingredients generally known in the field of the invention provided that the ingredients do not give harmful influence on the reaction.

Retinol derivatives according to the present invention can be utilized in the medicines, cosmetics, soap, shampoo and functional food in order to prevent and improve skin aging resulting in wrinkle, coarse skin, dryness and abnormal keratinization Pharmaceutical compositions comprising retinol derivatives of the present invention can be utilized as the agent for the treatment and the prevention of skin cancer, pimple and wrinkle with age, pigmentation, coarse skin and flappy skin. For the purpose of this invention, the methods of administration are to include oral, local, transdermal, intranasal, inhalation, ocular, rectal, intravenous, intraperitoneal, intramuscular, intraarterial, or subcutaneous route. Transdermal formulation such as lotion, ointment, gel, cream, patch or spray is derirable pharmaceutical formulation.

Even though recommended daily administration dosage is depend on the age, weight, disease of the patient, a suggested dose is 0.01 to 80 mg per kg body weight and 1 to 3 administration per day.

Also, cosmetic compositions containing retinol derivatives of the present invention can be added into the cosmetics in the purpose of the prevention and improvement of skin abnormality such as freckles, senile chromelasma. Cosmetic formulation such as toning lotion, nourishing lotion, massage cream, nourishing cream, pack, gel or skin adhesive type is desirable formulation but is not intended to limit in any way.

Also, food compositions containing retinol derivatives of the present invention can be added into various food, meat, chocolate, snack, cookies, pizza, instant noodles, ice creams, alcohol beverages, vitamins, health food in the purpose of the prevention and improvement of skin abnormality such as pimple, freckles, wrinkle, pigmentation, coarse skin and flappy skin.

EXAMPLE

Practical and presently preferred embodiments of the present inventions are illustrative as shown in the following Examples. However, this invention is not limited into these examples.

Example 1a

Preparation of (2E,4E,6E,8E)-3,7-dimethyl-9-(2,6,6-trimethyl-1-cyclohexenyl)-2,4,6,8-nonatetraenyl (3S)-4-[(1-benzyl-2-methoxy-2-oxoethyl)amino]-3-formylamino-4-oxobutanoate N-formyl-aspartam (843.3 mg), methylene chloride 10 ml and minimum amount of dimethylformamide (DMF) were added to nitrogen filled three mouth round bottom flask, and melted. The reaction mixture was cooled down into 0° C., 1-ethyl-3-(3-dimethylaminopropyl)carbodiimide hydrochloride [EDCI](683 mg) were added slowly, and stirred for approximately thirty minute. Retinol were added into the reaction mixture, small amount of N,N'-dimethylaminopyridine (DMAP) were added immediately, and stirred for approximately 1~3 hours. After the reaction were finished, eluent were removed under the low pressure, the residues were melted with ethyl acetate and washed several times with water and Brine. Organic phase were dried with anhydrous $MgSO_4$, concentrated under low pressure and separated with reverse-phase column chromatography.

yield: 82%

NMR data: 8.81(s, 1H), 7.12–7.13(t, 3H, J=7.08 Hz), 7.04(d, 2H, J=7.81 Hz), 6.64(dd, 1H, J=13.18 Hz), 6.27(d, 1H, J=15.14 Hz), 6.18(d, 1H, J=16.1 Hz), 6.11(d, 1H, J=11.72 Hz), 6.07(d, J=7.32 Hz), 5.56(t, J=7.32 Hz), 5.2(s, 1H), 4.75(d, J=7.32 Hz), 4.12(t, J=7.32 Hz), 3.70(s, 3H), 3.04(d, J=6.84 Hz), 2.94(dd, 2H, J=4.39 Hz), 2.65(d, 2H, J=6.84 Hz), 2.01(t, 2H, J=5.86), 1.95(s, 3H), 1.88(s, 3H), 1.17(s, 3H), 1.62(m, 2H), 1.46(m, 2H), 1.02(s, 6H)

Example 1b

Another Example of Example 1a

All procedure were done as Example 1a except utilization of N,N'-carbonyldiimidazole (CDI) as coupling reagent.

Example 1c

Another Example of Example 1a

All procedures were done as Example 1a except utilization of $SO_2Cl$ as coupling reagent.

Example 1d

Another Example of Example 1a

All procedure were done as Example 1a except utilization of N,N'-sulfuryldiimidazole (SDI) as coupling reagent.

Example 2

Preparation of (2E,4E,6E,8E)-3,7-dimethyl-9-(2,6,6-trimethyl-1-cyclohexenyl)-2,4,6,8-nonatetraenyl (3S)-4-[(1-benzyl-2-methoxy- 2-oxoethyl)amino]-3-amino-4-oxobutanoate. hydrochloride Aspartam.hydrochloride (150 mg), methylene chloride 10 ml and minimum amount of dimethylformamide (DMF) were added to nitrogen filled, three mouth-round bottom flask and melted. The reaction mixture was cooled down into 0° C., 1-ethyl-3-(3-dimethylaminopropyl)carbodiimide hydrochloride [EDCI](128 mg) were added slowly, and stirred for approximately 30 minutes. Retinol (130 mg) was added into the reaction mixture, small amount of N,N'-dimethylaminopyridine (DMAP) were added immediately, and stirred for approximately 1~3 hours. After the reaction was finished, eluent were removed under the low pressure, the residues were melted with ethyl acetate and washed several times with water and Brine. Organic phase were dried with anhydrous $MgSO_4$, concentrated under low pressure and separated with column chromatography.

yield: 62%

NMR data: 7.11–7.12(t, 3H, J=7.08 Hz), 7.0(d, 2H, J=7.81 Hz), 6.61(dd, 1H, J=13.18 Hz), 6.20(d, 1H, J=15.14 Hz), 6.10(d, 1H, J=16.1 Hz), 6.05(d, 1H, J=11.72 Hz), 6.02(d, J=7.32 Hz), 5.53(t, J=7.32 Hz), 5.10(bs, 1H), 4.70(d, J=7.32 Hz), 4.12(t, J=7.32 Hz), 3.70(s, 3H), 3.14(d, J=6.84 Hz), 2.84(dd, 2H, J=4.39 Hz), 2.45(d, 2H, J=6.84 Hz), 2.01(t, 2H, J=5.86), 1.75(s, 3H), 1.68(s, 3H), 1.17(s, 3H), 1.52(m, 2H), 1.26(m, 2H), 1.02(s, 6H)

Example 3

Preparation of Di[(2E,4E,6E,8E)-3,7-dimethyl-9-(2,6,6-trimethyl-1-cyclohexenyl)-2,4,6,8-nonatetraenyl] (2S)-2-[(tert-butoxycarbonyl)amino]butanedioate N-Boc aspartic acid (1.2 mg), methylene chloride 20 ml and minimum amount of dimethylformamide (DMF) were added to nitrogen filled, three mouth- round bottom flask and melted. The reaction mixture was cooled down into 0° C., 1-ethyl-3-(3-dimethylaminopropyl)carbodiimide hydrochloride [EDCI](1.36 g)were added slowly, and stirred for approximately 30 minutes. Retinol (0.51 g) was added into the reaction mixture, small amount of N,N'-dimethylaminopyridine (DMAP) were added immediately, and stirred for approximately 1~3 hours. After the reaction was finished, eluent were removed under the low pressure, the residues were melted with ethyl acetate and washed several times with water and Brine. Organic phase were dried with anhydrous $MgSO_4$, concentrated under low pressure and separated with column chromatography.

yield: 53%

NMR data: 6.64(dd, 3H, J=13.18 Hz), 6.23(d, 2H, J=15.14 Hz), 6.07(d, 2H, J=16.11 Hz), 6.05(d, 2H, J=11.23 Hz), 5.54(t, 2H, J=6.60 Hz), 4.77(d, 2H, J=7.23 Hz), 4.71(d, 2H, J=7.32 Hz), 2.97(dd, 2H, J=4.39 Hz), 2.01(t, 4H, J=5.86 Hz), 1.95(s, 6H), 1.88(s, 6H), 1.17(s, 6H), 1.62(m, 4H), 1.46(m, 4H), 1.42(s, 9H), 1.02(s, 12H)

Example 4

Preparation of Di[(2E,4E,6E,8E)-3,7-dimethyl-9-(2,6,6-trimethyl-1-cyclohexenyl)2,4,6,8-nonatetraenyl] (2S)-2-aminobutanedioate Aspartic acid (160 mg), N,N'-dicyclohexylcarbodiimide (DCC) (720 mg), methylene chloride 10 ml and minimum amount of dimethylformamide (DMF) were added to nitrogen filled, three mouth- round bottom flask and melted. Small amount of N,N'-dimethylaminopyridine (DMAP) were added. Retinol (324 mg) was added into the reaction mixture, and stirred for approximately 1~3 hours. After the reaction was finished, eluent were removed under the low pressure, the residues were melted with ethyl acetate and washed several times with water and Brine. Organic phase were dried with anhydrous $MgSO_4$, concentrated under low pressure and separated with column chromatography.

yield: 50%

NMR data: 6.54(dd, 3H, J=13.18 Hz), 6.08(d, 2H, J=15.14 Hz), 6.07(d, 2H, J=16.11 Hz), 6.05(d, 2H, J=11.23 Hz), 5.54(t, 2H, J=6.60 Hz), 4.57(d, 2H, J=7.23 Hz), 4.51(d, 2H, J=7.32 Hz), 2.67(dd, 2H, J=4.39 Hz), 2.01(t, 4H, J=5.86 Hz), 1.95(s, 6H), 1.88(s, 6H), 1.17(s, 6H), 1.62(m, 4H), 1.46(m, 4H), 1.02(s, 12H)

Example 5

Preparation of Di[(2E,4E,6E,8E)-3,7-dimethyl-9-(2,6,6-trimethyl-1-cyclohexenyl)-2,4,6,8-nonatetraenyl] 2-(acetylamino)succinate N-acetyl aspartic acid (610 mg), N,N'-dicyclohexylcarbodiimide (DCC) (720 mg), methylene chloride 10 ml and minimum amount of dimethylformamide (DMF) were added to nitrogen filled, three mouth- round bottom flask and melted. Small amount of N,N'-dimethylaminopyridine (DMAP) were added. Retinol (324 mg) was added into the reaction mixture, and stirred for approximately 1~3 hours. After the reaction was finished, eluent were removed under the low pressure, the residues were melted with ethyl acetate and washed several times with water and Brine (20 ml×2). Organic phase were dried with anhydrous $MgSO_4$, concentrated under low pressure and separated with column chromatography.

yield: 50%

NMR data: 6.54(dd, 3H, J=13.18 Hz), 6.08(d, 2H, J=15.14 Hz), 6.07(d, 2H, J=16.11 Hz), 6.05(d, 2H, J=11.23 Hz), 5.54(t, 2H, J=6.60 Hz), 4.57(d, 2H, J=7.23 Hz), 4.51(d, 2H, J=7.32 Hz), 2.67(dd, 2H, J=4.39 Hz), 2.01(t, 4H, J=5.86 Hz), 1.95(s, 6H), 1.88(s, 6H), 1.17(s, 6H), 1.62(m, 4H), 1.46(m, 4H), 1.42(s, 9H), 1.02(s, 12H)

Example 6

Preparation of (2E,4E,6E,8E)-3,7-dimethyl-9-(2,6,6-trimethyl-1-cyclohexenyl)-2,4,6,8-nonatetraenyl (9Z,11E)-9,11-octadecadienoate 1-ethyl-3-(3-dimethylaminopropyl) carbodiimide hydrochloride [EDCI] (0.71 g, 3.67 mmol) and anhydrous methylene chloride 15 ml were added to nitrogen filled, three mouth- round bottom flask and melted. The reaction mixture was cooled down into 0° C. Conjugated linoleic acid was added, and stirred for approximately 30 minutes. Retinol (0.87 g, 3.05 mmol) and N,N'-dimethylaminopyridine (DMAP) solubilized in anhydrous methylene chloride 7 ml were added into the reaction mixture, and stirred for 4 hours at room temperature. Organic phase were washed with water (20 ml×2) and brine (20 ml×2) and dried with anhydrous $MgSO_4$, concentrated under low pressure and separated with column chromatography (solvent:ethylacetate/hexane=1/8).

yield: 80%

NMR data(400 MHz, $CDCl_3$): 6.64(dd, 1H, J=15.14 Hz, 11.23 Hz), 6.29(d, 1H, J=15.14 Hz), 6.17(d, 1H, J=16.11 Hz), 6.12(d, 1H, J=16.11 Hz), 6.09(d, 1H, J=11.23 Hz), 5.96(m, 1H, J=10.74 Hz, 5.86 Hz), 5.93(m, 1H, J=10.74 Hz), 5.61(m, 1H, J=6.83 Hz, 7.32 Hz), 5.32(t, 1H, J=7.32 Hz), 5.30(m, 1H, J=10.74 Hz, 6.83 Hz), 4.72(d, 2H, J=7.32 Hz), 2.30(t, 2H, J=5.86 Hz), 2.14(m, 2H, J=5.86 Hz, 10.74 Hz), 2.08(m, 2H, J=5.86 Hz, 7.32 Hz), 2.01(m, 2H, J=5.86 Hz), 1.96(s, 3H), 1.89(s, 3H), 1.71(s, 3H), 1.60(m, 2H, J=5.86 Hz), 1.47(m, 2H, J=5.86 Hz), 1.29(n, 16H, J=5.86 Hz), 1.02(s, 16H), 0.87(t, 3H, J=7.32 Hz)

Example 7

Preparation of Di[(2E,4E,6E,8E)-3,7-dimethyl-9-(2,6,6-trimethyl-1-cyclohexenyl)-2,4,6,8-nonatetraenyl] malate 1-ethyl-3-(3-dimethylaminopropyl)carbodiimide hydrochloride [EDCI] (334.6 mg, 1.75 mmol) and anhydrous methylene chloride 5 ml were added to nitrogen filled, three mouth- round bottom flask and melted. The reaction mixture was cooled down into 0° C. Maleic acid (78 mg, 0.58 mmol) was added, and stirred for approximately 30 minutes. Retinol (500 mg, 1.75 mmol) and N,N'-dimethylaminopyridine solubilized in anhydrous methylene chloride 6 ml were added into the reaction mixture, and stirred for 4 hours at room temperature. Organic phase were washed with water (20 ml×2) and brine (20 ml×2) and dried with anhydrous $MgSO_4$, concentrated under low pressure and separated with column chromatography (solvent:ethylacetate/hexane=1/30).

yield: 48%

NMR data(400 MHz, $CDCl_3$): 6.60(dd, 2H, J=15.14 Hz, 11.23 Hz) 6.23 (d, 2H, J=15.14 Hz), 6.17(d, 2H, J=16.11 Hz), 6.13(d, 2H, J=16.11 Hz), 6.07(d, 2H, J=11.23 Hz), 5.50(t, 2H, J=7.32 Hz), 4.73(d, 2H, J=7.32 Hz), 4.65(d, 2H, J=7.32 Hz), 5.23(bq, 1H, J=16.60 Hz), 3.00(d, 1H, J=16.60 Hz), 2.90(d, 1H, J=16.60 Hz), 1.98(m, 4H, J=5.86 Hz), 1.94(s, 6H), 1.83(s, 6H), 1.68(s, 6H), 1.61(m, 4H, J=5.86 Hz), 1.46(m, 4H, J=5.86 Hz), 1.02(s, 12H)

Example 8

Preparation of Di[(2E,4E,6E,8E)-3,7-dimethyl-9-(2,6,6-trimethyl-1-cyclohexenyl)-2,4,6,8-nonatetraenyl] (E)-2-butenedioate 1-ethyl-3-(3-dimethylaminopropyl)carbodiimide hydrochloride [EDCI] (1.4 g, 7.32 mmol) and anhydrous methylene chloride 20 ml were added to nitrogen filled, three mouth- round bottom flask and melted. The reaction mixture was cooled down into 0° C. Fumalic acid (0.39 g, 3.05 mmol) was added, and stirred for approximately 30 minutes. Retinol (1.75 g, 6.10 mmol) and N,N'-dimethylaminopyridine solubilized in anhydrous methylene chloride 7 ml were added into the reaction mixture, and stirred for 4 hours at room temperature. Organic phase were washed with water (20 ml×2) and brine (20 ml×2) and dried with anhydrous $MgSO_4$, concentrated under low pressure and separated with column chromatography (solvent:ethylacetate/hexane=1/30).

yield: 50%

NMR data: 6.86(s, 2H), 6.65(dd, 2H, J=24 Hz), 6.08~6.29 (m, 8H), 5.63(t, 2H, J=15 Hz), 4.85(d, 4H, J=15 Hz), 1.99~2.03(m, 4H), 1.96(s, 6H), 1.91(s, 6H), 1.70(s, 6H), 1.59~1.62(m, 4H), 1.45~1.47(m, 4H), 1.02(s, 12H)

Example 9

Preparation of Di[(2E,4E,6E,8E)-3,7-dimethyl-9-(2,6,6-trimethyl-1-cyclohexenyl)-2.4,6,8-nonatetraenyl] (E)-2-methyl-2-butenedioate 1-ethyl-3-(3-dimethylaminopropyl) carbodiimide hydrochloride [EDCI] (1.4 g, 7.32 mmol) and anhydrous methylene chloride 20 ml were added to nitrogen filled, three mouth- round bottom flask and melted. The reaction mixture was cooled down into 0° C. Mesaconic acid (0.39 g, 3.05 mmol) was added, and stirred for approximately 30 minutes. Retinol (1.75 g, 6.10 mmol) and N,N'-dimethylaminopyridine solubilized in anhydrous methylene chloride 7 ml were added into the reaction mixture, and stirred for 4 hours at room temperature. Organic phase were washed with water (20 ml×2) and brine (20 ml×2) and dried with anhydrous $MgSO_4$, concentrated under low pressure and separated with column chromatography (solvent:ethylacetate/hexane=1/30).

yield: 53%

NMR data: 6.79(s, 1H), 6.65(dd, 2H, J=27 Hz), 6.08~6.29 (m, 8H), 5.63(t, 2H, J=14 Hz), 4.83(dd, 4H, J=16 Hz), 2.29(s, 3H, J=4.39 Hz), 1.99~2.03(m, 4H), 1.96(s, 6H), 1.91(s, 6H), 1.67(s, 6H), 1.58~1.62(m, 4H), 1.45~1.47(m, 4H), 1.02(s, 12H)

Example 10

Preparation of (1E,3E,5E,7E)-9[(2E,4E,6E,8E)-3,7-dimethyl-9-(2,6,6-trimethyl-1-cyclohexenyl)-2,4,6,8-nonatetraenyl]oxy-3,7-dimethyl-1-(2,6,6-trimethyl-1-cyclohexenyl)-1,3,5,7-nonateraene Retinol (0.6 g, 2.10 mmol), DEAD (Diethylazodicarboxylate) (0.3 g, 1.15 mmol), $Ph_3P$ (0.33 g, 1.15 mmol) and anhydrous methylene chloride 20 ml were added to nitrogen filled, three mouth- round bottom flask, melted and vigorously stirred for approximately 20 minutes. After the reaction was finished, 50 ml of water were added into the reaction mixture and ethylacetate (30 ml×2) was used for extraction. Organic phase were washed with water (50 ml) and brine (50 ml) and dried with MgSO$_4$, concentrated under low pressure and separated with column chromatography (solvent:ethylacetate/hexane=1/1).

yield: 84%

NMR data: 6.05(q, 4H, J=16.11 Hz), 5.14(br s, 6H), 4.16(q, 4H, J=7.32 Hz), 1.99(s, 6H), 1.74(s, 6H), 1.68(s, 6H), 1.63(t, 4H, J=5.86 Hz), 1.45(m, 4H), 1.01(s, 6H), 1.00(s, 6H)

Experimental Example 1

Cell Toxicity Test of Retinol-N-formyl-aspartam)

The cell line utilized for cell toxicity test of retinal derivatives were SK-Hep-1(liver cancer), MDA-MB-231 (breast cancer), HaCAT (skin cancer), and HCT116 (colon cancer). Those cell lines were maintained and cultured in DMEM (Dulbecco's Modified Eagle's Medium)/10% FBS containing 10% fetal bovine serum (FBS) (GibcoBRL, Gaithersburg, Md.). 3×10$^3$ cells, 100 µl media per well were distribute into 96 well microtiter plate and cultured for 24 hours. Each cultured cell lines were treated with various concentrations of retinal derivatives (0, 500, 1000, 5000 nM) for 4 days and living cells were counted with hemocytometer to measure the inhibition effect of cell proliferation.

The retinal derivatives utilized for the experiments were retinol-(N-formyl-aspartam), retinol, 4-HPR[N-(4-hydroxyphenyl)retineamide] (Sigma Co., St. Louis, Mo.). Those derivatives were eluted in dimethylsulfoxide and the concentration of dimethylsulfoxide added into culture media was kept at not over 0.01%.

Figure 1:
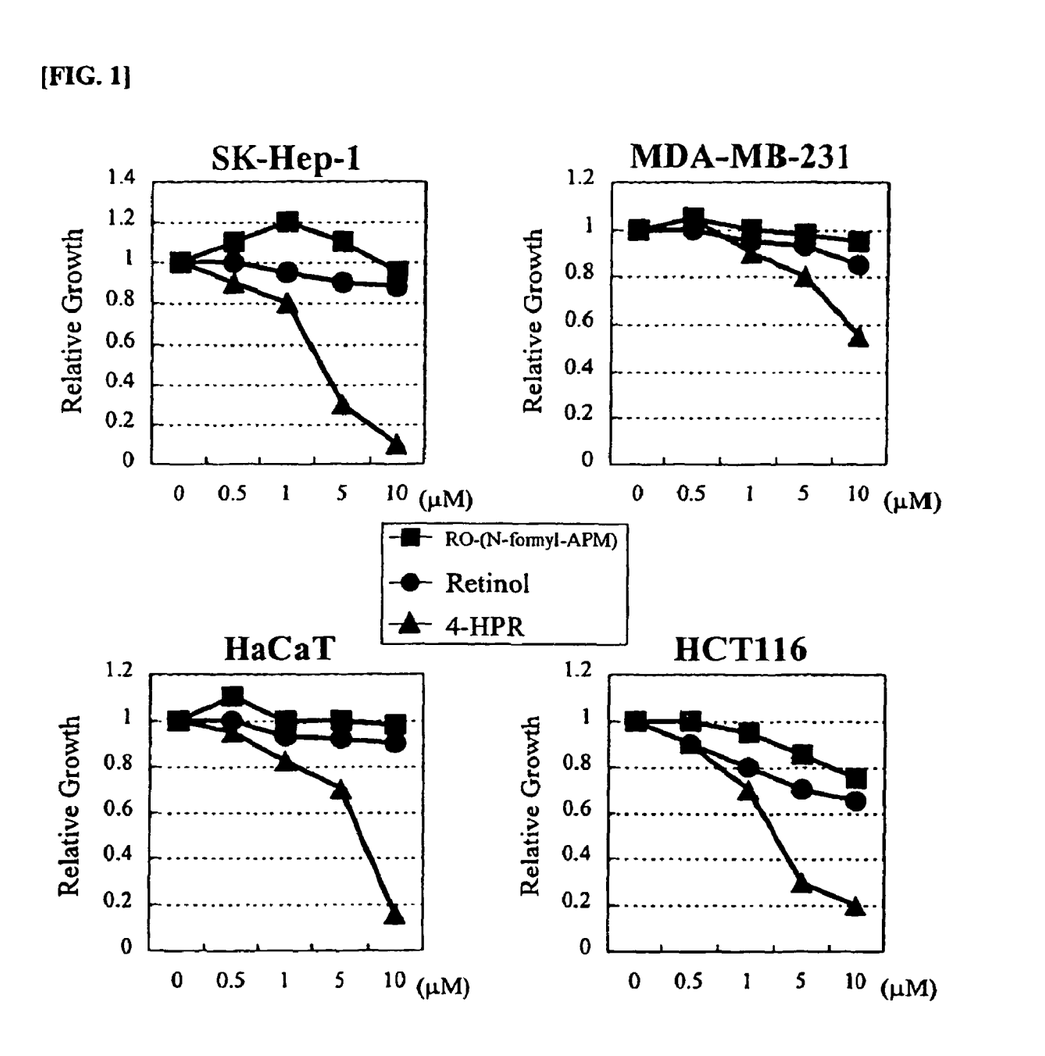
FIG. 1 shows the cell toxicity analysis of retinol-(N-formyl-aspartam) of this invention.

As shown in FIG. 1, the result of treatment with different concentration of the retinal derivatives were as following. Retinol-(N-formyl-aspartam) shows no toxicity on the SK-Hep-1 (liver cancer), MDA-MB-231 (breast cancer), and HaCAT (skin cancer) cell line, and show less toxicity than retinol on HCT116 (colon cancer) cell line.

Experimental Example 2

Activity Test of Retinoic Acid Receptor/Retinoid X Receptor (RAR/RXR) Using Retinol-(N-formyl-aspartam)

To analyze the effects of retinol-(N-formyl-aspartam) on the activity of retinoic acid receptor, skin cancer (HaCAT) cell lines were utilized to measure the activity of retinoic acid receptor/retinoid X receptor.

Recombinant DNA, DR5-tk-CAT or DR1-tk-CAT consisting of DR1 or DR5, effectors of retinoic acid receptor/retinoid X receptor, thymine kinase promoter, and CAT (chloramphenicol acetyl transferase) were mixed with the plasmid DNA expressing retinoic acid receptor α, β, γor retinoid X receptor α, β, γto cotransfect skin cancer (HaCAT) cell line with lipofectamine (GibcoBRL). The cotransfected cell lines were cultured for 1 day on DMEM/10% FBS media, each retinol derivatives (1 µM) were added and cultured for one more day, 5% CO$_2$, 37° C. The cells were washed with phosphate-buffered saline (PBS), and the proteins were isolated from each cells, and the activity of β-galactosidase and protein contents were measured to determine transfection efficacy, the transcription level of RAR or RXR receptor were measured with CAT ELISA (Roche Molecular Biochemical, Mannheim, Germany).

To determine the effect of retinol-(N-formyl-aspartam) on retinoic acid receptors, each retinoic acid receptor (α, β, or γ) expression vector and activity measuring DR5-tk-CAT plasmid were introduced with liposome. After treating cells with retinol-(N-formyl-aspartam), the cell extracts were isolated. The expression level of CAT were measured with CAT ELISA to determine the effect of retinol-(N-formyl-aspartam) on the activity of retinoic acid receptors.

Figure 2:
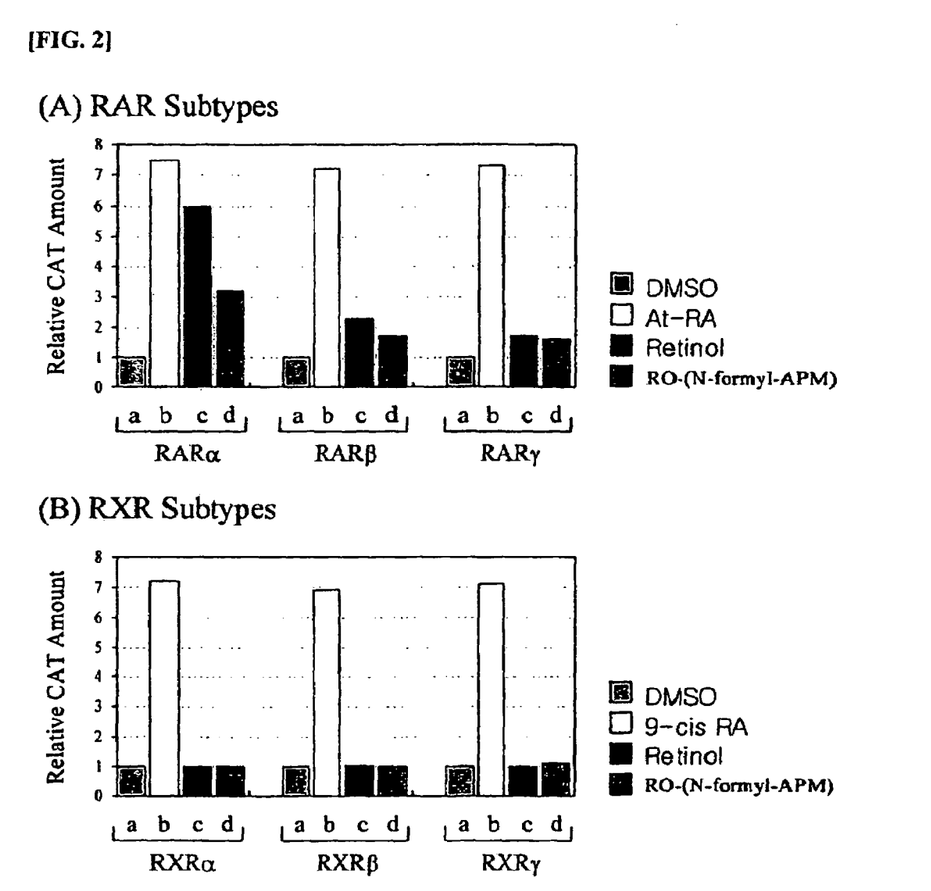
FIG. 2 shows the activity control analysis of retinol-(N-formyl-aspartam) of this invention on retinoic acid receptor/retinoid X receptor (RAR/RXR).

As shown in FIG. 2, retinol-(N-formyl-aspartam) resulted high activation of retinoic acid receptor a as retinol, shows weak activation of retinoic acid receptor β, γ(A). Retinol and retinol-(N-formyl-aspartam) derivatives resulted no activation of retinoid X receptor (α, β, γ) (B).

Experimental Example 3

Activity Test of Retinoic Acid Receptor (RAR) Treated with Retinol-(Mesaconic Acid)

To analyze the effects of retinol-(mesaconic acid) on the activity of retinoic acid receptor, Cos-1 cell line was utilized to measure the activity of retinoic acid receptor/retinoid X receptor.

Recombinant DNA, DR5-tk-CAT consisting of DR5, effectors of retinoic acid receptor/retinoid X receptor, thymine kinase promoter, and CAT (chloramphenicol acetyl transferase) were mixed with the plasmid DNA expressing retinoic acid receptor α, β, γand utilized to cotransfect skin cancer (HaCAT) cell line with lipofectamine (GibcoBRL). The cotransfected cell lines were cultured for 1 day on DMEM/10% FBS media, each retinol derivatives (1 µM) were added and cultured for one more day, 5% CO$_2$, 37° C. The cells were washed with phosphate-buffered saline (PBS), and the proteins were isolated from each cells, and the activity of β-galactosidase and protein contents were measured to determine transfection efficacy, the transcription level of RAR receptor were measured with CAT ELISA.

Figure 3:
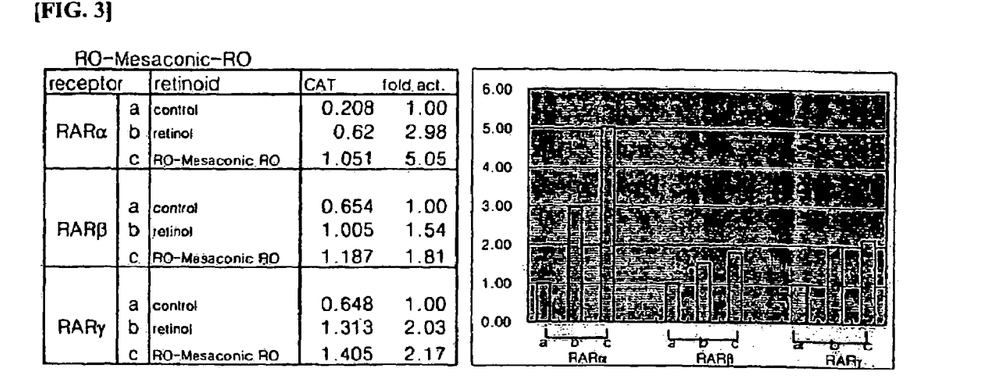
FIG. 3 shows the activity control analysis of retinol-mesaconic acid of this invention on retinoic acid receptor (RAR)

As shown in FIG. 3, retinol-(mesaconic acid) resulted in high activation of retinoic acid receptor α as retinol, and resulted in weak activation of retinoic acid receptor β, γin general.

Experimental Example 4

Activity Test of Retinoic Acid Receptor (RAR) Using Retinol-(Fumalic Acid)

To analyze the effects of retinol-(fumalic acid) on the activity of retinoic acid receptor, Cos-1 cell lines were utilized to measure the activity of retinoic acid receptor. All procedures were done as Experimental Example 3.

Figure 4:
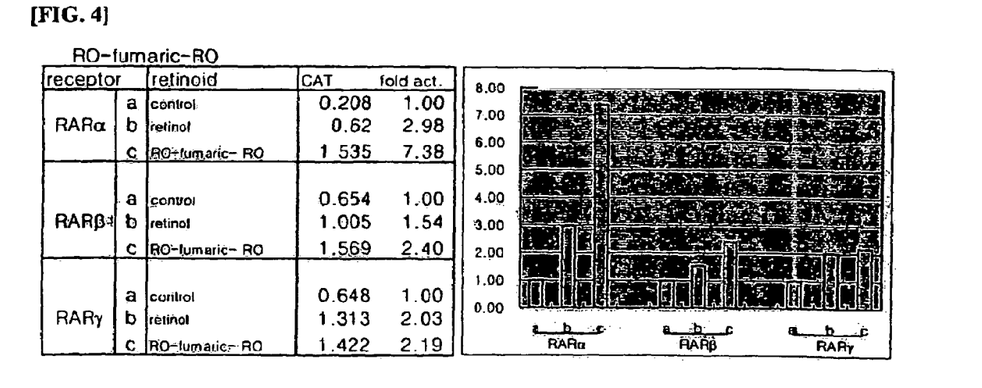
FIG. 4 shows the activity control analysis of retinol-fumaric acid of this invention on retinoic acid receptor (RAR)

As shown in FIG. 4, retinol-(fumalic acid) resulted in high activation of retinoic acid receptor α as retinol, and showed weak activation of retinoic acid receptor β, γ.

Experimental Example 5

Activity Test of Retinoic Acid Receptor (RAR) Using Retinol-(Retinol)

To analyze the effects of retinol-(retinol) on the activity of retinoic acid receptor, Cos-1 cell lines were utilized to measure the activity of retinoic acid receptor. All procedures were done as Experimental Example 3.

Figure 5:
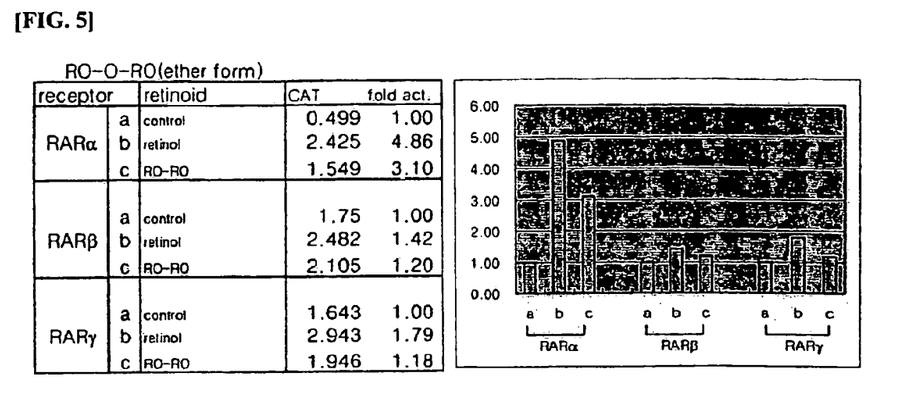
FIG. 5 shows the activity control analysis of retinol-retinol of this invention on retinoic acid receptor (RAR)

As shown in FIG. 5, retinol-(retinol) resulted in high activation of retinoic acid receptor α as retinol, and showed weak activation of retinoic acid receptor β, γ.

Experimental Example 6

Activity Inhibition Test of Activation Protein-1 (AP-1) Treated with Retinol-(N-formyl-aspartam)

Since the activation protein-1 (c-Jun is the constituent of AP-1) is transcription factor inducing expression of collagenase enzyme, which is a major cause of skin wrinkle, the effect of wrinkle prevention was determined by the activity inhibition test of AP-1.

CAT reporter (Coll-CAT) containing collagen promoter including AP-1 transcription factor binding site (TRE) were utilized to cotransfect skin cancer (HaCAT) cell line. The effect of retinol derivatives on the activity of AP-1 was measured by CAT ELISA. In some cases, the vector expressing c-Jun or retinoic acid receptors were utilized to cotransfect, and the effect of retinol derivatives on the transcription activity of c-Jun was analyzed.

With the assumption of the prepared retinol-(N-formyl-aspartam) derivatives which inhibit the activity of AP-1 causing skin wrinkle, would have the utility for cosmetics, the related investigations were proceeded. Similar to the experiment of retinoic acid receptor, AP-1 (c-jun) expression vector and Coll-CAT plasmid for the activity measurement were introduced into the skin cancer (HaCAT) cell line with liposome. After treating the cells with retinol-(N-formyl-aspartam) derivatives, the cell extracts were isolated. The expression level of CAT were measured with CAT ELISA to determine the effect of retinol-(N-formyl-aspartam) on the activity of the AP-1.

Figure 6:
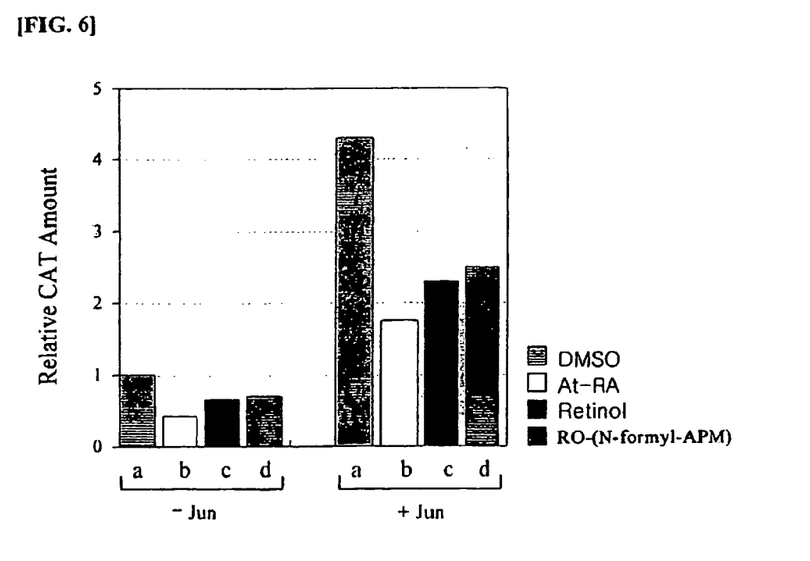
FIG. 6 shows the activity control analysis of retinol-(N-formyl-aspartam) of this invention on activation protein-1 (AP-1).

As shown in FIG. 6, the expression of c-Jun elevated the expresson of collagenase causing skin wrinkle, approximately 4.5 times, the treatment with retinol in the presence of retinoic acid receptor a lowered the expresson of collagenase approximately 47%. The treatment of retinoic acid or the retinol-(N-formyl-aspartam) lowered those approximately 60%, 44%, accordingly. In other cases, the similar inhibition ratios were obtained (FIG. 6, –c-Jun or +c-Jun). Therefore, those result showed that retinol-(N-formyl-aspartam) shows the similar inhibition effect on AP-1 activity as retinol, but less than retinoic acid

Experimental Example 7

Activity Inhibition Test of Activation Protein-1 (AP-1) Treated with Retinol-(Mesaconic Acid)

CAT reporter (Coll-CAT) containing collagen promoter including AP-1 transcription factor binding site (TRE) was utilized to transfect Cos-1 cell line. Activity inhibition tests of activation protein-1 (AP-1) similar to the experimental example 6 were proceeded.

When the expresson level of collagenase in the presence of the c-Jun expression was set as 100%, The treatment with retinol-(N-formyl-aspartam), retinoic acid, or retinol-(mesaconic acid) lowered the expresson of collagenase approximately 42%, 50%, or 30%, respectively. Therefore, those result showed that retinol-(mesaconic acid) has less effect on AP-1 activity inhibition than retinoic acid or retinol.

Experimental Example 8

Activity Inhibition Test of Activation Protein-1: AP-1 Using Retinol-(Fumalic Acid)

CAT reporter (Coll-CAT) containing collagen promoter including AP-1 transcription factor binding site (TRE) was utilized to transfect Cos-1 cell line. Activity inhibition tests of activation protein-1 (AP-1) similar to the experimental example 6 were proceeded.

When the expression level of collagenase in the presence of the c-Jun expression was set as 100%, the treatment with retinol-(fumalic acid) or retinoic acid lowered the expression of collagenase approximately 42%, 50% respectively. Therefore, those result showed that retinol-(fumalic acid) has no significant effect on AP-1 activity inhibition than retinoic acid or retinol.

Experimental Example 9

Activity Inhibition Test of Activation Protein-1: AP-1 Using Retinol-(Retinol)

CAT reporter (Coll-CAT) containing collagen promoter including AP-1 transcription factor binding site (TRE) was utilized to transfect Cos-1 cell line. Activity inhibition tests of activation protein-1 (AP-1) similar to the experimental example 6 were proceeded.

When the expression level of collagenase in the presence of the c-Jun expression was set as 100%, the treatment with retinol, retinoic acid or retinol-(retinol) lowered the expression of collagenase approximately 43%, 47.5%, 41.5% respectively. Therefore, those result showed that retinol-(retinol) has similar effect on AP-1 activity inhibition compared to retinoic acid or retinol.

INDUSTRIAL UTILITY

The retinol derivatives of this invention showed better stability against light than the retinol of prior art, which was known to be maintained without any alteration even after 10 days.

The retinol derivatives of this invention resulted in the high activation of retinoic acid receptor α as retinol, the weak activation of retinoic acid receptor β, γ in general and no activation of retinoid X receptor (α, β, γ).

Also, in the case of inhibition of activation protein-1, the retinol derivatives of this invention resulted in similar inhibition of c-jun activity as retinol, similar to the effect on retinoic acid receptor α.

Therefore, The retinol derivatives of this invention can be used effectively as a medication, cosmetic, soap, shampoo, functional food for the purpose of prevention and improvement of skin ageing caused by wrinkle, roughness, dryness, abnormal keratinization.

The invention claimed is:

1. A retinol derivative having formula (I):

wherein:

R¹ is H, CHO, retinoic acid, acetate or tert-butoxycarbonyl;

R² is OH, OCH₃, OC₂H₅, retinol or conjugated linoleic acid; and n is the integer of 1–6.

2. A retinol derivative comprising a carboether linkage between retinol and a peptide, wherein said peptide is selected from the group consisting of di-, tri- and polypeptide comprising α-aspartyl-L-phenylalanine-1-methylester (APM; aspartam), N-protecting group-aspartam and neotam.

3. A retinol derivative comprising a carboester linkage between retinol and an amino acid said retinol derivative having formula (II):

(II)

wherein:

R¹ is H, CHO, retinoic acid, acetate or tert-butoxycarbonyl;

R² is OH, OCH₃, OC₂H₅, retinol or conjugated linoleic acid; and n is the integer of 1–6.

4. The retinol derivative of claim 3, wherein said amino acid is selected from the group consisting of aspartic acid, N-protecting-aspartic acid, glutamic acid, N-protecting-glutamic acid, α-aspatyl-L-phenylalanine (α-AP) and N-protecting-α-aspatyl-L-phenylalanine.

5. A retinol derivative having formula (III):

(III)

wherein n=5.

6. A retinol derivative comprising a carboester linkage between retinol and a moiety having two carboxyl groups and one double bond, said retinol derivative having formula (IV):

(IV)

wherein:

R is H, CH₃ or C₂H₅.

7. The retinol derivative of claim 6, wherein said moiety is selected from the group consisting of maleic acid, fumaric acid and mesaconic acid.

8. A method for preparing retinol carboester derivative comprising the steps of:

(1) obtaining pure retinol by:
  a) combining of retinyl acetate with an inorganic salt in a methanolic solvent;
  b) extracting of a product of step 1a by an ether solvent;

(2) obtaining retinol carboester derivatives by:
  a) combining a compound selected from the group consisting of a peptide selected from the group consisting of di-, tri- and polypeptide comprising α-aspartyl-L-phenylalanine-1-methylester(APM; aspartam), N-protecting group-aspartam and neotam, an amino acid having two carboxyl groups, a moiety having carboxyl group and multiple double bonds on a carbon chain and a moiety having two carboxyl groups and one double bond on a carbon chain, with a condensing agent and methylene chloride to activate the acidity of the selected compound;
  b) adding retinol to the reaction mixture of step 2a in the presence of a catalyzing agent; and (3) separating obtained retinol carboester derivatives by column chromatography using a silicagel.

9. The method according to claim 8 or wherein the ether solvent is diethylether or tetrahydrofuran (THF).

10. The method according to claim 8, wherein the condensing agent is selected from the group consisting of N,N'-dicyclohexylcarbodiimide (DCC), 1-ethyl-3-(3-dimethylaminopropyl) carbodiimide hydrochloride (EDCI), N,N'-carbonyldiimidazole (CDI), N,N'-sulfryldiimidazole (SDI), and SO₂Cl.

11. A pharmaceutical composition comprising retinol derivatives of any one of claims 1 to 5, 6 or 7, and a pharmaceutically acceptable carrier, excipient or diluent.

12. A cosmetic composition comprising retinol derivatives of any one of claims 1 to 5, 6 or 7, and a carrier, excipient or diluent.

13. A soap or shampoo composition comprising retinol derivatives of any one of claims 1 to 5, 6 or 7, and a carrier, excipient or diluent.

14. A food composition comprising retinol derivatives of any one of claims 1 to 5, 6 or 7, and a food.

* * * * *